United States Patent [19]
Lakhani et al.

[11] Patent Number: 5,647,354
[45] Date of Patent: Jul. 15, 1997

[54] ARTIFICIAL RESPIRATION BAG

[75] Inventors: Mukund Lakhani, Beilstein; Jörg Brokelmann, Heilbronn-Biberach; Armin Singvogel, Remseck, all of Germany

[73] Assignee: Willy Rüsch AG, Kernen-Rommelshausen, Germany

[21] Appl. No.: 647,521

[22] Filed: May 15, 1996

[30] Foreign Application Priority Data

May 16, 1995 [DE] Germany .............. 195 17 857.235

[51] Int. Cl.$^6$ ................................................. A62B 9/04
[52] U.S. Cl. .............................. 128/205.13; 128/202.27
[58] Field of Search ........... 128/204.18, 202.28–203.11, 128/205.13–205.17, 202.27

[56] References Cited

U.S. PATENT DOCUMENTS

| | | | |
|---|---|---|---|
| 2,788,001 | 4/1957 | Brown | 128/205.17 |
| 3,097,642 | 7/1963 | Russell | 128/205.17 |
| 3,156,238 | 11/1964 | Bird et al. | 128/205.15 |
| 3,262,446 | 7/1966 | Stoner . | |
| 3,291,121 | 12/1966 | Vizneau | 128/205.15 |
| 3,773,045 | 11/1973 | Bova | 128/205.17 |
| 3,859,997 | 1/1975 | Deuma et al. | 128/205.17 |
| 3,960,148 | 6/1976 | Dryden | 128/205.17 |
| 4,244,363 | 1/1981 | Moore, Jr. et al. . | |
| 5,520,173 | 5/1996 | Kuhn | 128/205.14 |

FOREIGN PATENT DOCUMENTS 4409076  5/1995  Germany .

OTHER PUBLICATIONS

"Neuer Beatmungsbeutel von Söhngen", In: Biotechnische Umschau 3 (1979), vol. 1, pp. 20–21.
ISO 5362, Anaesthetic reservoir bags, Second edition, 15 Sep. 1986, (Ref.No. ISO5362-1986(E); pp. 1–3.

*Primary Examiner*—Kimberly L. Asher
*Attorney, Agent, or Firm*—Paul J. Vincent

[57] ABSTRACT

An artificial respiration bag (10) comprises an inflatable sidewardly folded reservoir (11). A holding element (12) and a support (15) forming a lumen opening (16) and connected to a cuff (13) are provided for on the reservoir. The entire artificial respiration bag (10) is produced from a silicone or thermoplastic elastomer. In this manner, the artificial respiration bag (10) is manufactured from a material to which the skin is insensitive and which does not cause allergic reactions. The holding element (12) has an integrally vulcanized holding ring (12'). The support (15) has a surrounding enlargement (20) which engages a shoulder (19) of the cuff and is permanently attached thereto. In this manner, the artificial respiration bag (10) fulfills the strength and safety requirements of ISO-standard 5362.

4 Claims, 1 Drawing Sheet

U.S. Patent   Jul. 15, 1997   5,647,354

ARTIFICIAL RESPIRATION BAG

BACKGROUND OF THE INVENTION

The invention concerns an artificial respiration bag, comprising an inflatable sidewards folded reservoir having a holding element and a support forming an opening volume which is connected to a cuff.

This type of respiration bag, made from rubber, is utilized for artificial respiration.

Artificial respiration is necessary in the event that an injured or sick individual is no longer capable of sufficient independent breathing, i.e. of taking-in sufficient oxygen and giving-off sufficient carbon dioxide. Artificial respiration is normally used in conjunction with anaesthesia.

Artificial respiration is possible both with and without an artificial respiration apparatus. One type of artificial respiration involves the use of an artificial respiration bag. The artificial respiration bag is folded at its side and can be inflated and collapsed to effect the artificial respiration. Conventional artificial respiration bags have a cuff with which the artificial respiration bag is connected to an oxygen feed-line and with which it can be connected to a breathing mask. The artificial respiration bag is hand-operatable and is standard equipment in ambulances, operation rooms and the like.

The conventional respiration bag is made from rubber in order to be able to manufacture the artificial respiration bag with sufficient safety and strength, in particular in the strongly loaded transition region between the reservoir and the cuff and in the vicinity of the holding element. Due to its rubber elastic properties, the conventional respiration bag satisfies the requirements of ISO-standard 5362 which must be fulfilled by this type of respiration bag.

The conventional artificial respiration bag made from rubber has, however, the disadvantage that contact therewith can lead to allergic or over-sensitive reactions both in the patient as well as in the responsible physician or nursing staff. In the event that the conventional respiration bag is made from latex or from a similar material, latex allergies can occur.

The conventional artificial respiration bag made from rubber or latex has the additional disadvantage that this type of material ages and suffers from a reduction in its elasticity after a certain amount of use. As a result there is a tendency for the conventional artificial respiration bag to crack or tear after a certain period of time.

It is therefore the underlying purpose of the present invention to further improve the conventional artificial respiration bag in such a fashion that it is manufactured from a material to which the skin is insensitive, which does not cause any allergic reactions, and which also fulfills the strength and safety requirements of ISO-standard 5362.

SUMMARY OF THE INVENTION

This purpose is achieved in accordance with the invention in that the entire artificial respiration bag is made from silicone or from a thermoplastic elastomer and the holding element comprises an integrally vulcanized holding ring with the support having a peripheral enlargement which engages a shoulder of the cuff and is permanently attached thereto.

Due to the utilization of material made from silicone, the artificial respiration bag in accordance with the invention has a constant elasticity both at low as well as at high temperatures. The artificial respiration bag in accordance with the invention is heat-insensitive and also hydrophobic.

Since the artificial respiration bag in accordance with the invention comprises only components that are made from silicone, it is highly biologically compatible and does not tend to cause allergic reactions. Due to the use of silicone, the artificial respiration bag in accordance with the invention can also be sterilized a plurality of times.

Artificial respiration bags of prior art were not made from silicone, since silicone, compared to rubber, does not have a high degree of stretchability without tearing. In particular, the utilization of silicone in the vicinity of the holding element and the cuff of the artificial respiration bag was associated with significant problems due to the high material load in these regions. If, however, the holding element comprises an integrally vulcanized holding ring which, for example, is formed in an extrusion process, i.e. during manufacture of the artificial respiration bag, the artificial respiration bag in accordance with the invention achieves high strength in this region to withstand large loads. The integrally vulcanized holding ring can, in particular, be made from silicone, a thermoplastic, an elastomer, a metal or a ceramic. The holding ring facilitates a strengthening of the holding element. This type of strengthening can also be achieved by integrally vulcanized elements having a geometrical shape different from that of a holding ring. Since the support, which forms the opening volume of the artificial respiration bag reservoir, engages a shoulder of the cuff and is firmly connected to this shoulder, the artificial respiration bag in accordance with the invention has an advantageous combination of strength and elasticity even in this second particularly stressed region, to guarantee a stable opened lumen. For this reason the artificial respiration bag made from silicone satisfies the requirements of ISO-standard 5362. A secure connection between the support and the cuff can be achieved, for example, using a glue connection or through welding.

The ISO-standard has specifications concerning the leakage rate of the artificial respiration bag. Previous use of silicone in an artificial respiration bag was associated with leakage rate difficulties caused by the formation of cracks in the transitional region between the reservoir and the holding element and the cuff. The artificial respiration bag in accordance with the invention also satisfies the leakage rate requirements of ISO-standard 5362 due to the construction, in accordance with the invention, of these regions. This is particularly important when treating a patient with an anaesthetic gas.

In a particularly preferred embodiment of the present invention, the holding ring comprises nubs distributed around the outer periphery and is made from a material having a higher Shore A or D hardness than the reservoir. The formed nubs make it possible to insert the holding ring into a mold to be completely surrounded by injected material during molding for interlocked joining to the reservoir. In this manner a single component artificial respiration bag is made which has an exceptionally good combination of strength and elasticity in the vicinity of the holding element. This is increased to an even greater extent in the event that the holding ring is manufactured from a material which is harder than the reservoir.

In the event that the holding ring is made from a material having a hardness of 70 Shore A, the holding element has a resistance to tearing sufficiently high to prevent formation of tears in the vicinity of the holding element during proper use of the artificial respiration bag in accordance with the invention.

In the event that the reservoir is manufactured from a material having a hardness between 20 to 70 Shore A the reservoir is easily inflatable and can be easily deflated through pushing together with the hands.

Further advantages can be derived from the description and the accompanying drawing. The above mentioned features as well as those to be further explained below can be utilized in accordance with the invention individually or collectively in arbitrary combination. The embodiments mentioned are not to be considered as exhaustive enumerations, rather have exemplary character only.

The invention is represented in the drawing and is further explained in connection with the embodiments.

DESCRIPTION OF THE PREFERRED EMBODIMENT

Figure 1:
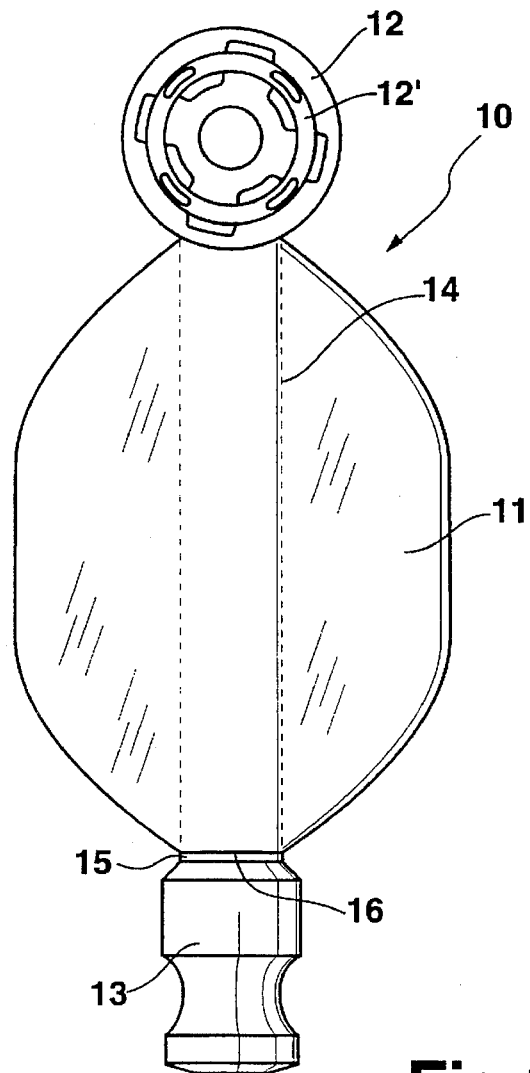
FIG. 1 shows a side view of an artificial respiration bag in accordance with the invention.

The individual figures of the drawing show the object in accordance with invention in a partially highly schematic fashion and should not be taken to scale.

FIG. 1 shows a side view of the artificial respiration bag 10 in accordance with the invention. The artificial respiration bag 10 comprises a reservoir 11 which is connected to a holding element 12 and to a cuff 13. The holding element 12 is transparent and ring-shaped and has, as shown in the figure, an extruded holding ring 12' in its inner portion which is integrally vulcanized. The holding ring 12' causes the holding element 12 to have a particularly high resistance to tearing. The reservoir 11 is folded at the sides via two fold-lines 14 to provide for an inflatable and stretchable volume. A support 15 forms an opening volume 16 for the artificial respiration bag 10. The support 15 is firmly connected to the cuff 13.

Figure 2:
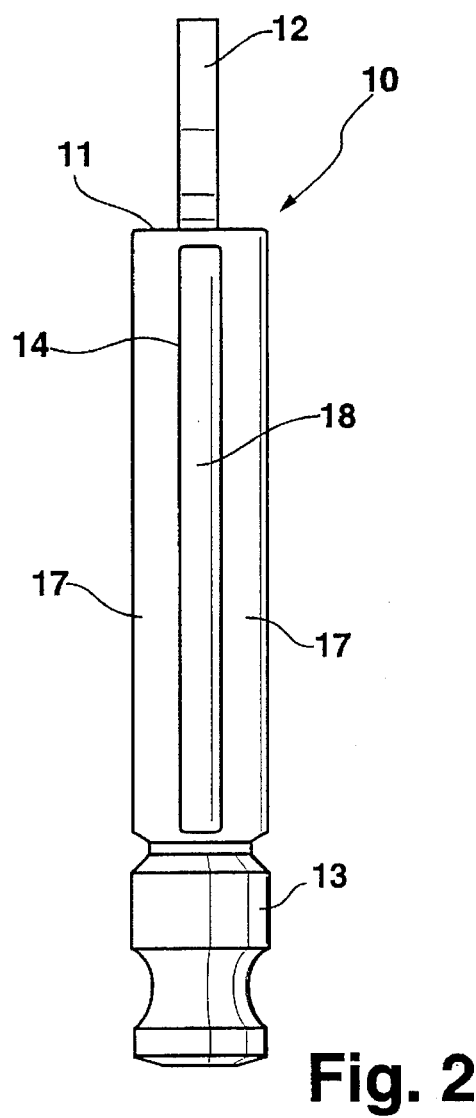
FIG. 2 shows a side view of the artificial respiration bag in accordance with the invention rotated by 90° relative to FIG. 1.

FIG. 2 shows an additional side view of the artificial respiration bag 10. The reservoir 11 is defined by side regions 17 which are separated from each other by inwardly folded folding region 18. The folding region 18 can be inwardly folded at folding lines 14. The holding element 12 is formed on one end of the reservoir 11 and the reservoir 11 is firmly connected to the cuff 13 at the other end.

Figure 3:
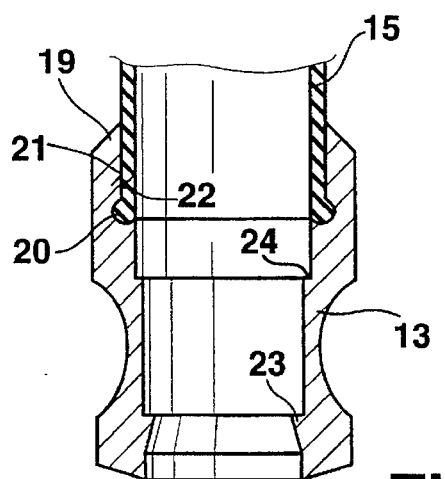
FIG. 3 shows a cut through a cuff of the artificial respiration bag according to FIGS. 1 and 2.

FIG. 3 shows an enlarged cut through the cuff 13. The cuff 13 has a section 19 facing the reservoir 11 which is engaged by an enlargement 20 extending around the support 15. The engagement of the enlargement 20 anchors the support 15 at the cuff 13. In this fashion, the outer wall 21 of the support 15 tightly seats on an inner wall 22 of the shoulder 19. The connection between the outer wall 21 and inner wall 22 can be effected by means of glueing, vulcanizing, or another method of connection so that the support 15 is firmly connected to the cuff 13. In addition, the cuff 13 has protrusions 23, 24 to facilitate engagement and holding of a cuff adapter introduced into the cuff 13. The support 15 can be additionally strengthened in the vicinity of the cuff 13 and/or thickened to further increase the resistivity to tearing of the connection and to guarantee a good seating of the cuff adapter piece.

Figure 4:
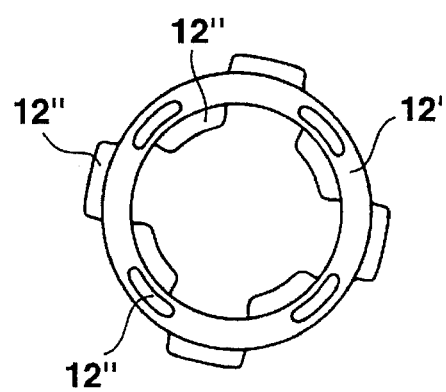
FIG. 4 shows a plan view of a holding ring having nubs distributed around its outer periphery.

FIG. 4 shows a holding ring 12' in an enlarged representation. Radially outwardly and radially inwardly protruding nubs 12'' are formed on the holding ring 12'. The nubs 12'' are also formed on the outer surface of the holding ring 12' in the axial direction.

An artificial respiration bag 10 comprises an inflatable sidewardly folded reservoir 11. A holding element 12 and a support 15 forming a lumen opening 16 and connected to a cuff 13 are provided for on the reservoir. The entire artificial respiration bag 10 is produced from a silicone or thermoplastic elastomer. In this manner, the artificial respiration bag 10 is manufactured from a material to which the skin is insensitive and which does not cause allergic reactions. The holding element 12 has an integrally vulcanized holding ring 12'. The support 15 has a surrounding enlargement 20 which engages a shoulder 19 of the cuff and is permanently attached thereto. For this reason the artificial respiration bag 10 fulfills the strength and safety requirements of ISO-standard 5362.

We claim:

1. An artificial respiration device comprising:
   a holding element consisting essentially of at least one of silicone and a thermoplastic elastomer;
   a holding ring integrally vulcanized in said holding element;
   a reservoir consisting essentially of at least one of silicone and a thermoplastic elastomer and integral with said holding element at a first end of said reservoir, said reservoir having side folds for inflation;
   a support consisting essentially of at least one of silicone and a thermoplastic elastomer and forming a lumen at a second end of said reservoir, said support having a peripheral enlargement; and
   a cuff consisting essentially of at least one of silicone and a thermoplastic elastomer, said cuff having a shoulder engaging and permanently attached to said peripheral enlargement.

2. The device of claim 1, wherein said holding ring has nubs distributed around an outer perimeter thereof, said holding ring consisting essentially of a material having a higher Shore A or D hardness than said reservoir.

3. The device of claim 2, wherein said holding ring consists essentially of a material with a hardness of 70 Shore A.

4. The device of claim 2, wherein said reservoir consists essentially of a material with a hardness between 20 to 70 Shore A.

* * * * *